(12) United States Patent  
Parquet et al.

(10) Patent No.: US 8,075,617 B2  
(45) Date of Patent: Dec. 13, 2011

(54) DEVICE FOR CONNECTION BETWEEN A HEART PROSTHESIS AND THE NATURAL AURICLES

(75) Inventors: Jean-Marc Parquet, Domont (FR); Alain Carpentier, Paris (FR); Pascal Bareau, Magny les Hameaux (FR); Antoine Capel, Clamart (FR)

(73) Assignee: Carmat, Paris (FR)

( * ) Notice: Subject to any disclaimer, the term of this patent is extended or adjusted under 35 U.S.C. 154(b) by 249 days.

(21) Appl. No.: 12/304,445

(22) PCT Filed: Jun. 11, 2007

(86) PCT No.: PCT/FR2007/000960  
§ 371 (c)(1),  
(2), (4) Date: Dec. 11, 2008

(87) PCT Pub. No.: WO2007/144496  
PCT Pub. Date: Dec. 21, 2007

(65) Prior Publication Data  
US 2009/0276041 A1    Nov. 5, 2009

(30) Foreign Application Priority Data  
Jun. 15, 2006 (FR) .................... 06 05332

(51) Int. Cl.  
*A61M 1/12* (2006.01)

(52) U.S. Cl. ......... 623/3.26; 623/3.1; 623/2.4; 623/2.41
(58) Field of Classification Search .................. None  
See application file for complete search history.

(56) References Cited

U.S. PATENT DOCUMENTS

| 4,981,484 A | * | 1/1991 | Holfert et al. ................ 623/3.21 |
| 5,135,539 A | | 8/1992 | Carpentier |
| 6,143,025 A | * | 11/2000 | Stobie et al. ................ 623/2.39 |

FOREIGN PATENT DOCUMENTS

| EP | 0 324 669 | 7/1989 |
| FR | 2 107 724 | 5/1972 |
| FR | 2 784 585 | 4/2000 |
| GB | 1 307 135 | 2/1973 |

OTHER PUBLICATIONS

International Search Report dated Oct. 17, 2007 w/ English translation.  
Written Opinion of the International Searching Authority with English translation.

* cited by examiner

*Primary Examiner* — David Isabella  
*Assistant Examiner* — Suba Ganesan  
(74) *Attorney, Agent, or Firm* — Dickinson Wright PLLC

(57) ABSTRACT

A device for connection between a heart prosthesis and a person's natural auricles includes a structure for joining to the natural auricles with individual suture attachments mounted so as to be free in rotation and movable.

6 Claims, 3 Drawing Sheets

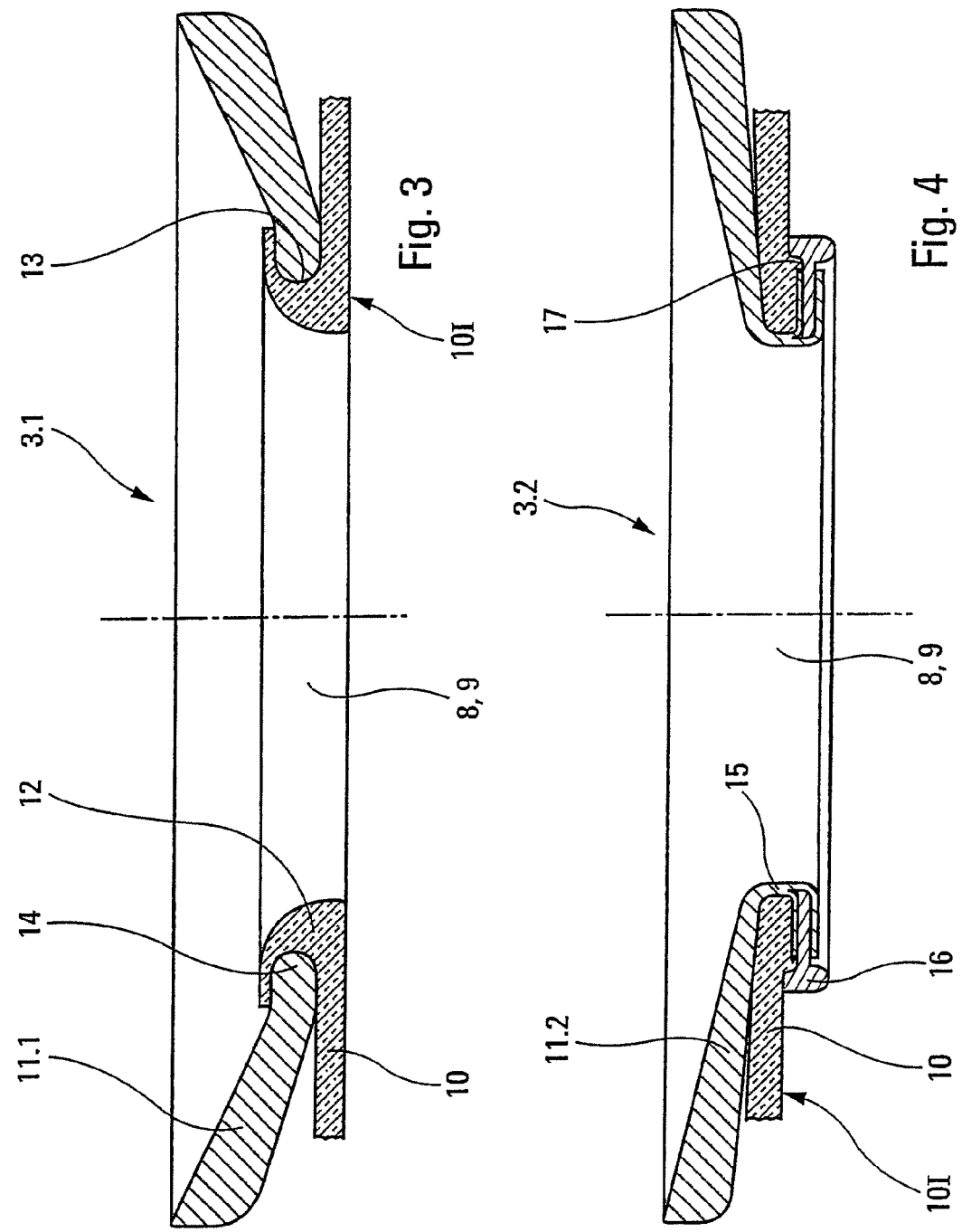

DEVICE FOR CONNECTION BETWEEN A HEART PROSTHESIS AND THE NATURAL AURICLES

FIELD OF THE INVENTION

The present invention relates to a device for connection between a heart prosthesis and the natural auricles.

BACKGROUND OF THE RELATED ART

Document U.S. Pat. No. 5,135,539 has already disclosed a heart prosthesis implantable in the pericardial cavity of a patient and able to replace the natural left and right ventricles of said patient after their removal. This heart prosthesis comprises a rigid body in which artificial left and right ventricles are arranged, said artificial ventricles being provided with means for rapid connection to the natural left and right auricles of said patient, comprising:
- a first bezel forming an integral part of said rigid body and comprising first and second orifices which communicate respectively with the artificial left ventricle and with the artificial right ventricle by way of valves;
- a second bezel comprising third and fourth orifices that can be connected respectively to said natural left auricle and to said natural right auricle.

In this embodiment, said first and second bezels can be connected to each other removably, in order to assume an operative position in which said first and third orifices are located opposite each other and said second and fourth orifices are located opposite each other.

Such a system of bezels greatly facilitates the connection of said prosthesis to said second bezel, previously connected to said natural auricles.

To connect said second bezel to the natural auricles, provision is made in document U.S. Pat. No. 5,135,539 to equip said third and fourth orifices with a suture ring on which said auricles are respectively sutured in a leaktight manner. However, given that said auricles are composed of flexible and easily deformable tissue and that they are not completely independent, since they are connected by the interauricular septum, it can happen that said auricles do not have the optimal orientation with respect to said second bezel to avoid torsion and compression. In this case, such defects in terms of orientation can be corrected only by new sutures after detachment of the auricles from said suture ring.

The object of the present invention is to overcome this disadvantage.

SUMMARY OF THE INVENTION

To this end, according to the invention, the heart prosthesis implantable in the pericardial cavity of a patient, said prosthesis being able to replace the natural left and right ventricles of said patient after their removal, and comprising a rigid body in which artificial left and right ventricles are arranged, said artificial ventricles being provided with means for rapid connection to the natural left and right auricles of said patient, comprising:
- a first bezel forming an integral part of said rigid body and comprising first and second orifices which communicate respectively with the artificial left ventricle and with the artificial right ventricle; and
- a second bezel comprising third and fourth orifices that can be connected respectively to said natural left auricle and to said natural right auricle, said third and fourth orifices being provided with joining means on which said natural auricles are respectively sutured in a leaktight manner, said first and second bezels being able to be connected to each other removably, in order to assume an operating position in which said first and third orifices are located opposite each other and said second and fourth orifices are located opposite each other, is distinguished by the fact that said joining means are formed by individual suture flanges mounted in such a way as to be free in rotation on said third and fourth orifices respectively.

It is thus possible to correct errors in the orientation of the auricles by simply rotating the flanges relative to said second bezel.

Moreover, it is advantageous that said individual suture flanges are mounted removably on said third and fourth orifices, respectively.

Thus, with said individual suture flanges being removable from the second bezel, the result is that the suturing of an auricle to a flange can be effected when the flange is momentarily separated from the second bezel, which may sometimes simplify the operation.

In a first embodiment of the invention, each individual suture flange comprises a central opening delimited by an inner peripheral edge, and said second bezel comprises, around each of said third and fourth orifices, an annular projection forming a groove inside of which said edge of said central opening is engaged.

Alternatively, each individual suture flange comprises a central opening delimited by a rim that can enclose the edge of the third or fourth orifice, respectively. In this case, it is advantageous that said ream of the suture flange has a peripheral continuation bearing against the inner face of said second bezel. Thus, the blood contained in the auricle has only a single material as interface. It is also advantageous that this continuation comprises, at its end, a ring made of elastic material, for example an elastomer, that can serve as a seal when it is pressed between said bezels in the connected position and contributes to the axial positioning of said flange with respect to the third or fourth orifice, respectively. For this purpose, the inner face of the second bezel can comprise an annular projection which surrounds said third or fourth orifice and behind which said elastic ring can fasten itself elastically.

BRIEF DESCRIPTION OF THE DRAWINGS

The figures in the attached drawing will show clearly how the invention can be realized. In these figures, identical reference signs designate similar elements.

FIGS. 3 and 4 illustrate, on a greater scale, two embodiments of suture flanges of said natural auricles.

DETAILED DESCRIPTION OF THE INVENTION

Figure 1:
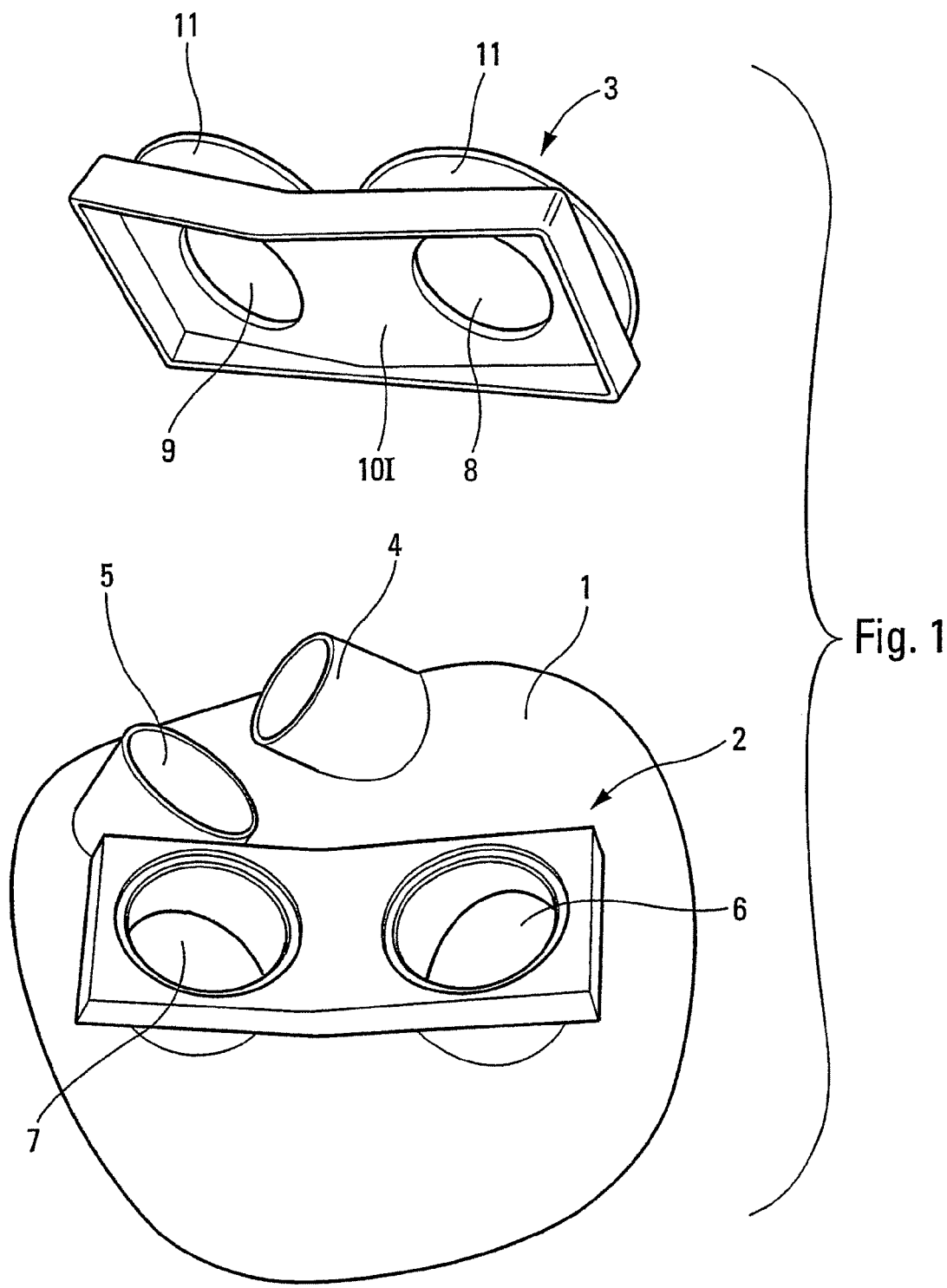
FIG. 1 is an exploded and schematic perspective view of a heart prosthesis according to the present invention.

The heart prosthesis according to the present invention, shown in FIG. 1 in an exploded view, is able to replace the natural left and right ventricles of a patient after their removal. It comprises a rigid body 1 in which artificial left and right ventricles (not visible in FIG. 1) are arranged, said ventricles being provided with means 2, 3 for connection to the natural left and right auricles (not visible) of said patient, and means 4, 5, respectively, for connection to the pulmonary artery and the aorta.

Figure 2:
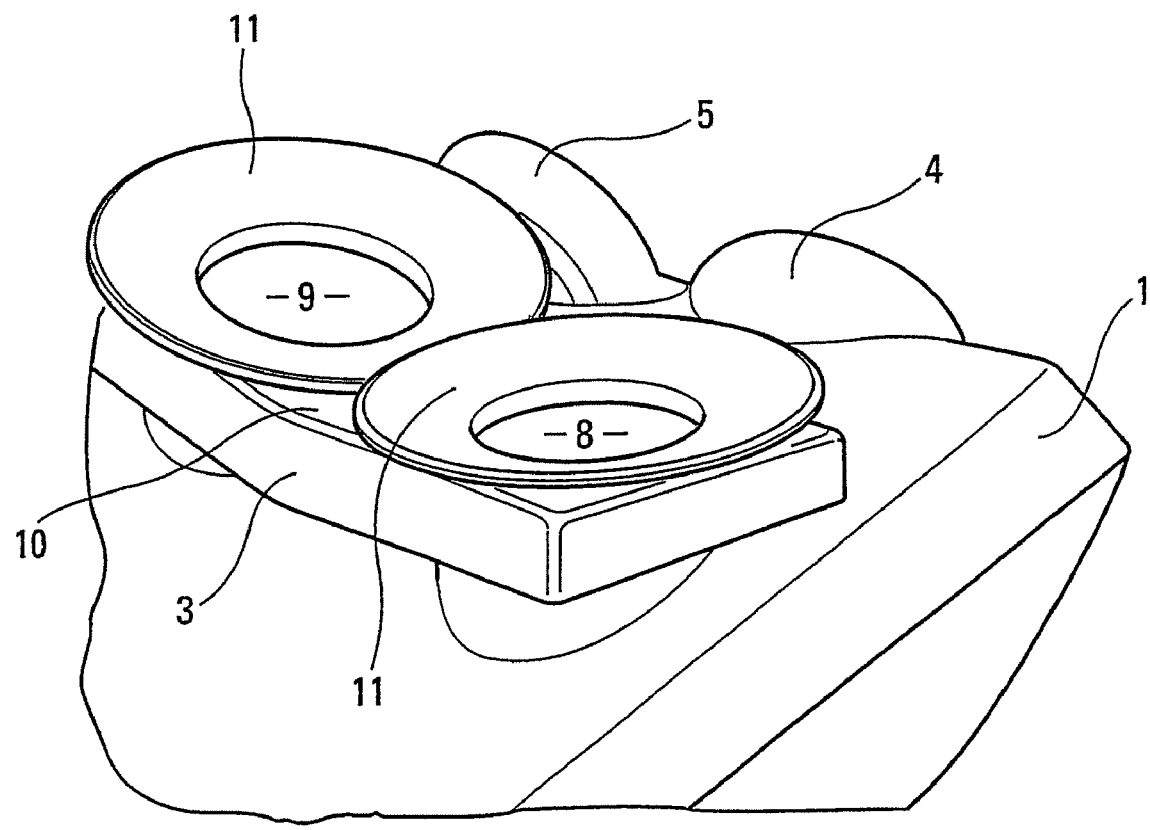
FIG. 2 is a perspective top view of part of the heart prosthesis from FIG. 1, mounted on the bezel for connection to the natural auricles.

The means for connection to said natural left and right auricles comprise:

a bezel 2 forming an integral part of said rigid body 1 and comprising an orifice 6 which communicates with the artificial right ventricle and an orifice 7 which communicates with the artificial left ventricle, valves (not shown in FIG. 1) being arranged in said orifices 6, 7; and a bezel 3 to which the bezel 2 can be connected removably and which comprises, in its wall 10, orifices 8, 9 that can be arranged opposite said orifices 6 and 7, respectively, when said bezels occupy the precise relative position corresponding to the functioning of the prosthesis (see FIG. 2).

Said bezels 2 and 3 have the general shape of right-angled parallelepipeds, and the bezel 3 can serve as a cover for the bezel 2.

In the operating position of the prosthesis, when said bezels 2 and 3 are engaged (see FIG. 2), they are locked in position by means not shown.

As can be seen from FIGS. 1 and 2, each orifice 8, 9 is equipped with an individual flange 11 that enables suturing of the corresponding natural auricle.

In the embodiment 3.1 of the bezel 3, represented in FIG. 3, around each orifice 8, 9 and located opposite the inner face 10I of the wall 10, there is an annular projection 12, which is provided with a peripheral groove 13. The corresponding embodiment 11.1 of the individual flange 11 comprises a central opening delimited by an inner peripheral edge 14 engaged in said peripheral groove 13.

It will be readily understood that, in the illustrative embodiment in FIG. 3, the individual flange 11.1 can easily turn around the corresponding orifice 8, 9, its inner peripheral edge 14 sliding in rotation in said peripheral groove 13. Moreover, the individual flange 11.1 can easily be mounted on and removed from the annular projection by elastic deformation of said inner peripheral edge 14.

In the embodiment 3.2 of the bezel 3, represented in FIG. 4, the orifices 8 and 9 are simple holes formed in the wall 10. By contrast, the embodiment 11.2 of each individual flange 11.2 comprises a central opening delimited by a rim 15 enclosing the edge of the corresponding orifice 8, 9 and bearing against the inner face 10I in such a way as to promote hemocompatibility by presenting only a single interface to the blood. Moreover, the rim 15 is continued peripherally by a ring 16 of elastic material, for example an elastomer, that can serve as a seal when it is crushed between the bezels 2 and 3 connected to each other. This ring 16 can also participate in the axial positioning of the flange 11.2 with respect to the corresponding orifice 8, 9. For this purpose, on said inner face 10I, an annular projection 17 can be provided which surrounds said orifices 8, 9 and behind which said elastic ring 16 can attach itself.

It will be noted that the individual flanges 11.2 can turn around the orifices 8, 9 and can be mounted thereon and removed therefrom by elastic deformation of the rim 15 and of the ring 16.

The individual suture flanges 11, 11.1, 11.2 can be made of any suitable hemocompatible material, for example multilayer material.

The invention claimed is:

1. A heart prosthesis implantable in the pericardial cavity of a patient, said prosthesis being able to replace the natural left and right ventricles of said patient after their removal, and comprising a rigid body in which artificial left and right ventricles are arranged, said artificial ventricles being provided with a structure for connection to the natural left and right auricles of said patient, comprising:

a first bezel forming an integral part of said rigid body and comprising first and second orifices, which communicate respectively with the artificial left ventricle and with the artificial right ventricle; and a second bezel comprising third and fourth orifices that can be connected respectively to said natural left auricle and to said natural right auricle, said third and fourth orifices being provided with a joining structure on which said natural auricles are respectively sutured in a leaktight manner, wherein:

said first and second bezels being able to be connected to each other removably, in order to assume an operative position in which said first and third orifices are located opposite each other and said second and fourth orifices are located opposite each other, said joining structure is formed by two individual suture flanges, each comprising a central opening, and said suture flanges are mounted by elastic deformation of said central openings on said third and fourth orifices, respectively, in such a way as to be removable therefrom and free in rotation thereon.

2. The heart prosthesis according to claim 1, wherein the central opening of each individual suture flange is delimited by an inner peripheral edge, and said second bezel comprises, around each of said third and fourth orifices, an annular projection forming a groove inside of which said edge of said central opening is engaged.

3. The heart prosthesis according to claim 1, wherein the central opening of each individual suture flange is delimited by a rim that can enclose the edge of the corresponding third and fourth orifices.

4. A heart prosthesis implantable in the pericardial cavity of a patient, said prosthesis being able to replace the natural left and right ventricles of said patient after their removal, and comprising a rigid body in which artificial left and right ventricles are arranged, said artificial ventricles being provided with a structure for connection to the natural left and right auricles of said patient, comprising:

a first bezel forming an integral part of said rigid body and comprising first and second orifices, which communicate respectively with the artificial left ventricle and with the artificial right ventricle; and a second bezel comprising third and fourth orifices that can be connected respectively to said natural left auricle and to said natural right auricle, said third and fourth orifices being provided with a joining structure on which said natural auricles are respectively sutured in a leaktight manner, wherein:

said first and second bezels being able to be connected to each other removably, in order to assume an operative position in which said first and third orifices are located opposite each other and said second and fourth orifices are located opposite each other, said joining structure is formed by two individual suture flanges, each comprising a central opening, the central opening of each individual suture flange is delimited by a rim that can enclose the edge of the corresponding third and fourth orifices, said rim of the suture flange bears against the inner face of said second bezel comprising said third and fourth orifices, and said suture flanges are mounted by elastic deformation of said central opening on said third and fourth orifices, respectively, in such a way as to be removable therefrom and free in rotation thereon.

5. The heart prosthesis according to claim 4, wherein said rim is continued peripherally by a ring of elastic material that cooperates with said inner face in order to ensure the axial positioning of said flange with respect to be corresponding orifice.

6. The heart prosthesis according to claim 5, wherein the inner face of said second bezel comprises an annular projection which surrounds said third or fourth orifice and behind which said elastic ring can fasten itself elastically.

* * * * *